United States Patent
Tutt et al.

(10) Patent No.: US 8,507,037 B2
(45) Date of Patent: *Aug. 13, 2013

(54) DIGITAL MANUFACTURE OF AN GAS OR LIQUID SEPARATION DEVICE

(75) Inventors: Lee W. Tutt, Webster, NY (US); Donna P. Suchy, Rochester, NY (US)

(73) Assignee: Eastman Kodak Company, Rochester, NY (US)

( * ) Notice: Subject to any disclaimer, the term of this patent is extended or adjusted under 35 U.S.C. 154(b) by 660 days.

This patent is subject to a terminal disclaimer.

(21) Appl. No.: 12/608,047

(22) Filed: Oct. 29, 2009

(65) Prior Publication Data

US 2011/0104386 A1    May 5, 2011

(51) Int. Cl.
 *B01D 15/08*    (2006.01)

(52) U.S. Cl.
 USPC ........... 427/244; 427/469; 427/470; 427/485; 427/195; 427/197; 427/261; 427/286; 427/375; 427/385.5; 427/407.1; 427/419.2; 427/419.5; 210/658

(58) Field of Classification Search
 USPC ................. 427/195, 197, 203, 469, 470, 485, 427/243–244, 261, 286, 375, 385.5, 407.1, 427/419.2, 419.5; 210/263, 656–659
 See application file for complete search history.

(56) References Cited

U.S. PATENT DOCUMENTS

| | | | |
|---|---|---|---|
| 4,965,131 A | 10/1990 | Nair et al. | |
| 5,778,295 A | 7/1998 | Chen et al. | |
| 6,086,825 A | 7/2000 | Sundberg et al. | |
| 6,567,641 B1 | 5/2003 | Aslam et al. | |
| 6,896,360 B2 | 5/2005 | Cox et al. | |
| 6,976,384 B2 | 12/2005 | Hobbs et al. | |
| 7,553,393 B2 | 6/2009 | Derand et al. | |
| 7,557,232 B2 | 7/2009 | Liu et al. | |
| 2008/0159786 A1 | 7/2008 | Tombs et al. | |
| 2008/0248370 A1* | 10/2008 | Abd Elhamid et al. | 429/34 |
| 2009/0142100 A1* | 6/2009 | Suchy et al. | 399/223 |

FOREIGN PATENT DOCUMENTS

| | | |
|---|---|---|
| EP | 0765763 | 4/1997 |
| WO | WO 88/10193 | 12/1988 |
| WO | WO 98/54004 | 12/1998 |
| WO | WO2008-082648 | 7/2008 |
| WO | WO2009/011773 | 1/2009 |

* cited by examiner

*Primary Examiner* — Michael Cleveland
*Assistant Examiner* — Alex A Rolland
(74) *Attorney, Agent, or Firm* — Donna P. Suchy (57) ABSTRACT

Printing one or more layers using toner and/or laminates to form one or more multi-channeled layers, with a particular pattern, including forming a desired image, for example, electrographically, on a receiver member. The multi layered channel printing apparatus and related method and print incorporates one or more static layers, and one or more moveable layers that allow a fluid to move through the micro channels via an opening or through a direct fill. It also incorporates particles in the channels to act as a packing material for separation of components of samples. The packing material can either be applied directly or using the electrographic printing process. An optional capping layer or substrate may then be applied.

20 Claims, 8 Drawing Sheets

DIGITAL MANUFACTURE OF AN GAS OR LIQUID SEPARATION DEVICE

CROSS REFERENCE TO RELATED APPLICATIONS

This application relates to commonly assigned, copending U.S. application Ser. No. 12/608,040, filed Oct. 29, 2009, entitled: "DIGITAL MANUFACTURE OF A MICROFLUIDIC DEVICE."

FIELD OF THE INVENTION

The present invention relates electrographic printing and more particularly to printing a three-dimensional micro-chromatography column.

BACKGROUND OF THE INVENTION

One common method for printing images on a receiver member is referred to as electrography. In this method, an electrostatic image is formed on a dielectric member by uniformly charging the dielectric member and then discharging selected areas of the uniform charge to yield an image-wise electrostatic charge pattern. Such discharge is typically accomplished by exposing the uniformly charged dielectric member to actinic radiation provided by selectively activating particular light sources in an LED array or a laser device directed at the dielectric member. After the image-wise charge pattern is formed, resin particles are given a charge, substantially opposite the charge pattern on the dielectric member and brought into the vicinity of the dielectric member so as to be attracted to the image-wise charge pattern to develop such pattern into a patterned image.

Thereafter, a suitable receiver member (e.g., a cut sheet of plain bond paper) is brought into juxtaposition with the marking particle developed image-wise charge pattern on the dielectric member. A suitable electric field is applied to transfer the marking particles to the receiver member in the image-wise pattern to form the desired print image on the receiver member. The receiver member is then removed from its operative association with the dielectric member and the marking particle print image is permanently fixed to the receiver member typically using heat, and/or pressure and heat. Multiple layers or marking materials can be overlaid on one receiver, for example, layers of different color particles can be overlaid on one receiver member to form a layer print image on the receiver member after fixing.

In the earlier days of electrographic printing it was desirable to minimize channel formation during fusing. Under most circumstances, channels are considered an objectionable artifact in the print image. In order to improve image quality, and still produce channels a new method of printing has been formulated in U.S. Publication 2009/0142100. In that invention one or more multi-channeled layers are formed using electrographic techniques. There, use of layered printing, includes possible raised images to create channels capable of allowing movement of a fluid, such as an ink or dielectric, to provide a printed article with, among other advantages, a variety of security features on a digitally printed document.

In copending application U.S. Ser. No. 12/608,040 microfluidic structures are used for transporting liquid materials around and mixing in a small device. The liquids are transported to sensors which are used to sense the materials. In microfluidics there is a need though to separate materials as well as mixing materials before the transport to the sensors. In some case it may be necessary to add components to only one component of a samples mixture for better detection.

Gas and liquid chromatography are well known separation techniques. In these techniques an unknown sample of materials are placed in a flowing stream through a channel containing a packing material/stationary phase and allowed to move through the channel. The packing material usually will have some affinity to the materials undergoing testing. Some examples of packing materials are described in Some U.S. Pat. No. 7,557,232. As the unknown materials flow through the channels they are slowed by this affinity to the packing material. Each material in the sample may have a slightly different affinity to the packing material and hence will move through the channel at a different rate. After a specific distance, if there is a difference in the affinity, the materials will have completely separated. A detector can then be used to detect the amount and may identify the material. If the affinities are similar between some components, then one solution is to use a second column of different packing material. Another solution is the reaction of some of the components to allow different affinities.

Microfluidics with laminates is known, as discussed in U.S. Pat. No. 7,553,393. In that patent there is no discussion of the method of manufacture of the channels. The inventors assume one has already generated it and present a lamination method.

Often times, there is also a need to have either multiple sensors to identify materials or to have redundancy. Some materials are difficult to detect by a particular technique. For example colorless materials are difficult to detect by visible absorption while others may have conductivities such that they can not adequately be distinguished from the carrier fluid. In these cases, it would be desirable to route the liquids to multiple sensors.

It would also be desirable to have a cheap configurable channel routing process for separation and detection processes in an inexpensive manner. To allow a small device it should also have the ability to interface well with microfluidic transport and mixing. This invention solves these problems.

SUMMARY OF THE INVENTION

In view of the above, this invention is directed to electrographic printing wherein toner and/or laminates form one or more multi-channeled layers, with a particular pattern, which can be printed by electrographic techniques. Such electrographic printing includes the steps of forming a desired image, electrographically, on a receiver member and incorporating channels that are embedded into the design.

The multi layered channel printing apparatus and related method and print incorporates one or more static layers, and one or more moveable layers that allow a fluid to move through the micro channels via an opening or through a direct fill. It also incorporates particles in the channels to act as a packing material for separation of components of samples. The packing material can either be applied directly or using the electrographic printing process. An optional capping layer or substrate may then be applied.

The invention, and its objects and advantages, will become more apparent in the detailed description presented below.

BRIEF DESCRIPTION OF THE DRAWINGS

The above and other objects, features, and advantages of the present invention will become more apparent when taken in conjunction with the following description and drawings wherein identical reference numerals have been used, where possible, to designate identical features that are common to the figures.

In the detailed description of the preferred embodiment of the invention presented below, reference is made to the accompanying drawings, in which.

DETAILED DESCRIPTION OF THE INVENTION

Figure 1:
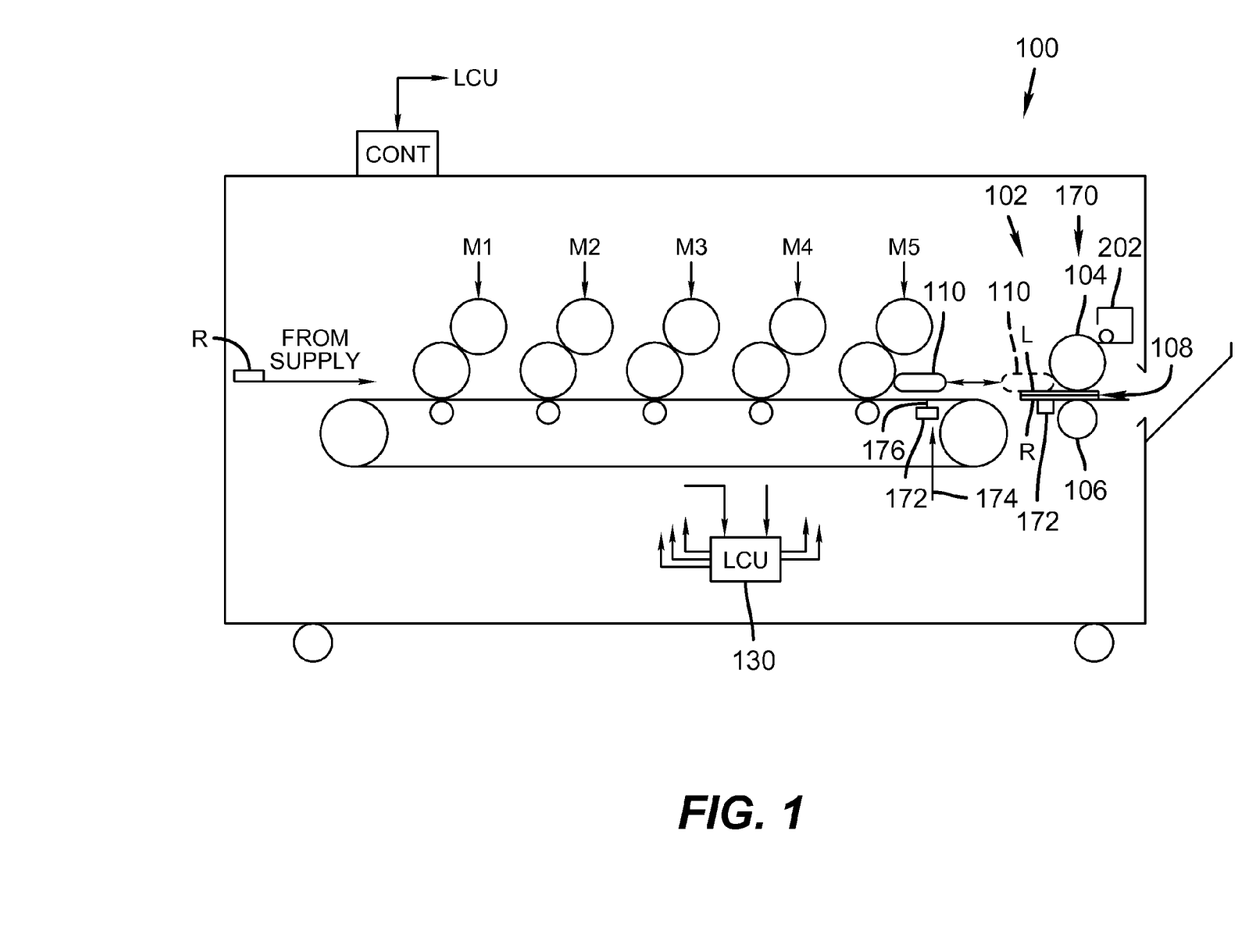
FIG. 1 is a schematic side elevational view, in cross section, of a typical electrographic reproduction apparatus suitable for use with this invention.
Figure 2:
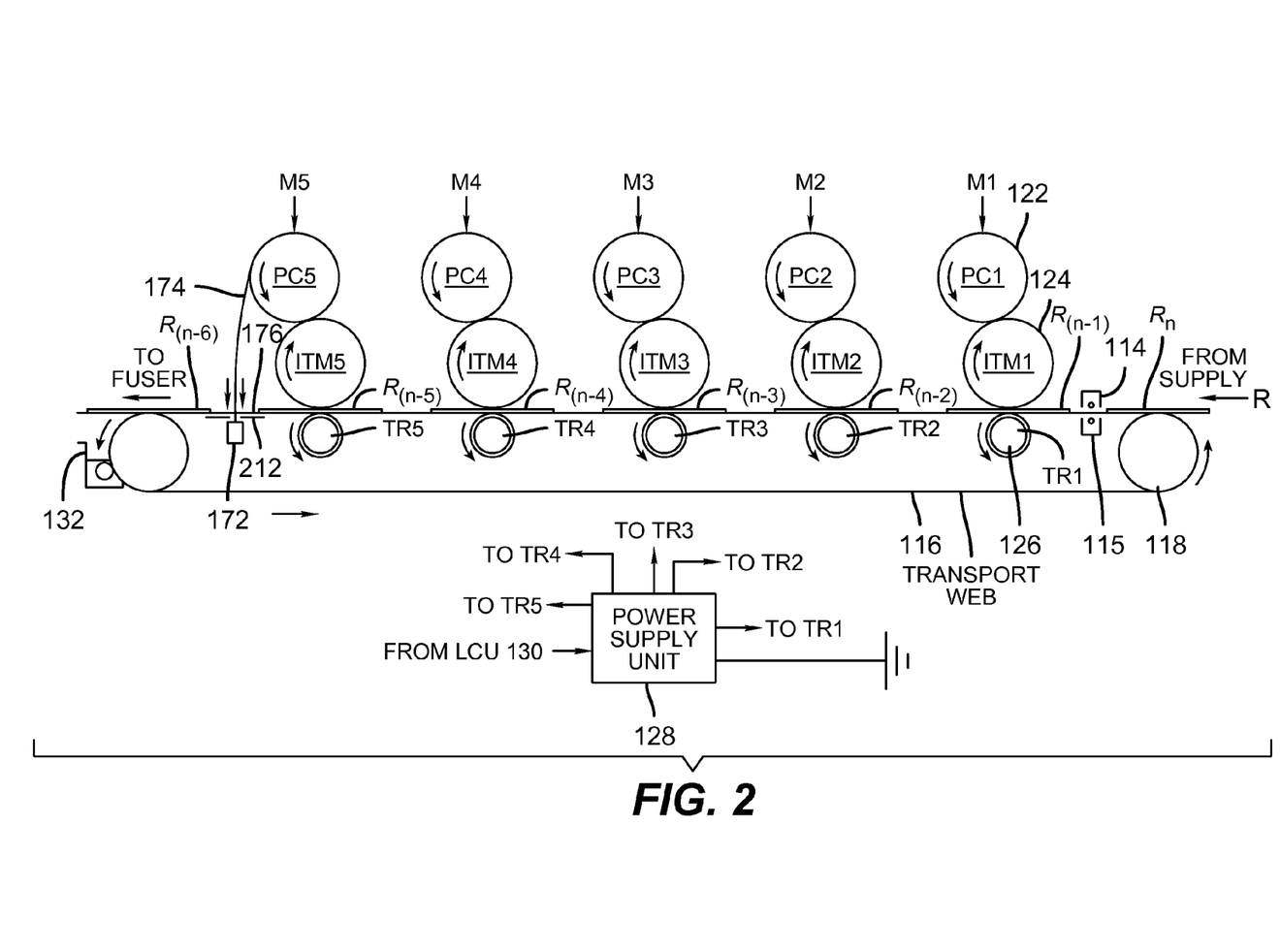
FIG. 2 is a schematic side elevational view, in cross section, of the reprographic image-producing portion of the electrographic reproduction apparatus of FIG. 1, on an enlarged scale.

Referring now to the accompanying drawings, FIGS. 1 and 2 are side elevational views schematically showing portions of a typical electrographic print engine or printer apparatus suitable for printing of multi-channel layered prints. One embodiment of the invention involves printing using an electrophotographic engine having five sets of single layer image producing or printing stations or modules arranged in tandem and an optional finishing assembly. The invention contemplates that more or less than five stations may be combined to deposit toner on a single receiver member, or may include other typical electrographic writers, printer apparatus, or other finishing devices.

An electrographic printer apparatus 100 has a number of tandemly arranged electrostatographic image forming printing modules M1, M2, M3, M4, and M5 and a finishing assembly 102. Additional modules may be provided.

Each of the printing modules generates a single-layer toner image for transfer to a receiver member successively moved through the modules. The finishing assembly has a fuser roller 104 and an opposing pressure roller 106 that form a fusing nip 108 there between. The finishing assembly 118 can also include a laminate application device 110. A receiver member R, during a single pass through the five modules, can have transferred, in registration, up to five single toner images to form a pentalayer image. As used herein, the term pentalayer implies that in an image formed on a receiver member combinations of subsets of the five layers are combined to form other layers on the receiver member at various locations on the receiver member, and that all five layers participate to form multiple layers in at least some of the subsets wherein each of the five layers may be combined with one or more of the other layers at a particular location on the receiver member to form a layer different than the specific layer toners combined at that location.

Receiver members (Rn-R(n–6), where n is the number of modules as shown in FIG. 2) are delivered from a paper supply unit (not shown) and transported through the printing modules M1-M5 in a direction indicated in FIG. 2 as R. The receiver members are adhered (e.g., preferably electrostatically via coupled corona tack-down chargers 114, 115) to an endless transport web 116 entrained and driven about rollers 118, 120. Each of the printing modules M1-M5 similarly includes a photoconductive imaging roller, an intermediate transfer member roller, and a transfer backup roller. Thus in printing module M1, a toner separation image can be created on the photoconductive imaging roller PC1 (122), transferred to intermediate transfer member roller ITM 1 (124), and transferred again to a receiver member moving through a transfer station, which includes ITM1 forming a pressure nip with a transfer backup roller TR1 (126).

Similarly, printing modules M2, M3, M4, and M5 include, respectively: PC2, ITM2, TR2; PC3, ITM3, TR3; PC4, ITM4, TR4; and PC5, ITM5, TR5. A receiver member, Rn, arriving from the supply, is shown passing over roller 118 for subsequent entry into the transfer station of the first printing module, M1, in which the preceding receiver member R(n–i) is shown. Similarly, receiver members R n–2) R(n) R(n–4), and R<n–5) are shown moving respectively through the transfer stations of printing modules M2, M3, M4, and M5. An unfused image formed on receiver member R (n–6) is moving, as shown, towards one or more finishing assemblies 118 including a fuser, such as those of well known construction, and/or other finishing assemblies in parallel or in series that includes, preferably a lamination device 110 (shown in FIG. 1). Alternatively the lamination device 110 can be included in conjunction to one of the print modules, Mn, which in one embodiment is the fifth module M5.

A power supply unit 128 provides individual transfer currents to the transfer backup rollers TR1, TR2, TR3, TR4, and TR5 respectively. A logic and control unit 130 (FIG. 1) in response to signals from various sensors associated with the electrophotographic printer apparatus 100 provides timing and control signals to the respective components to provide control of the various components and process control parameters of the apparatus in accordance with well understood and known employments. A cleaning station 132 for transport web 116 is also typically provided to allow continued reuse thereof.

Figure 3:
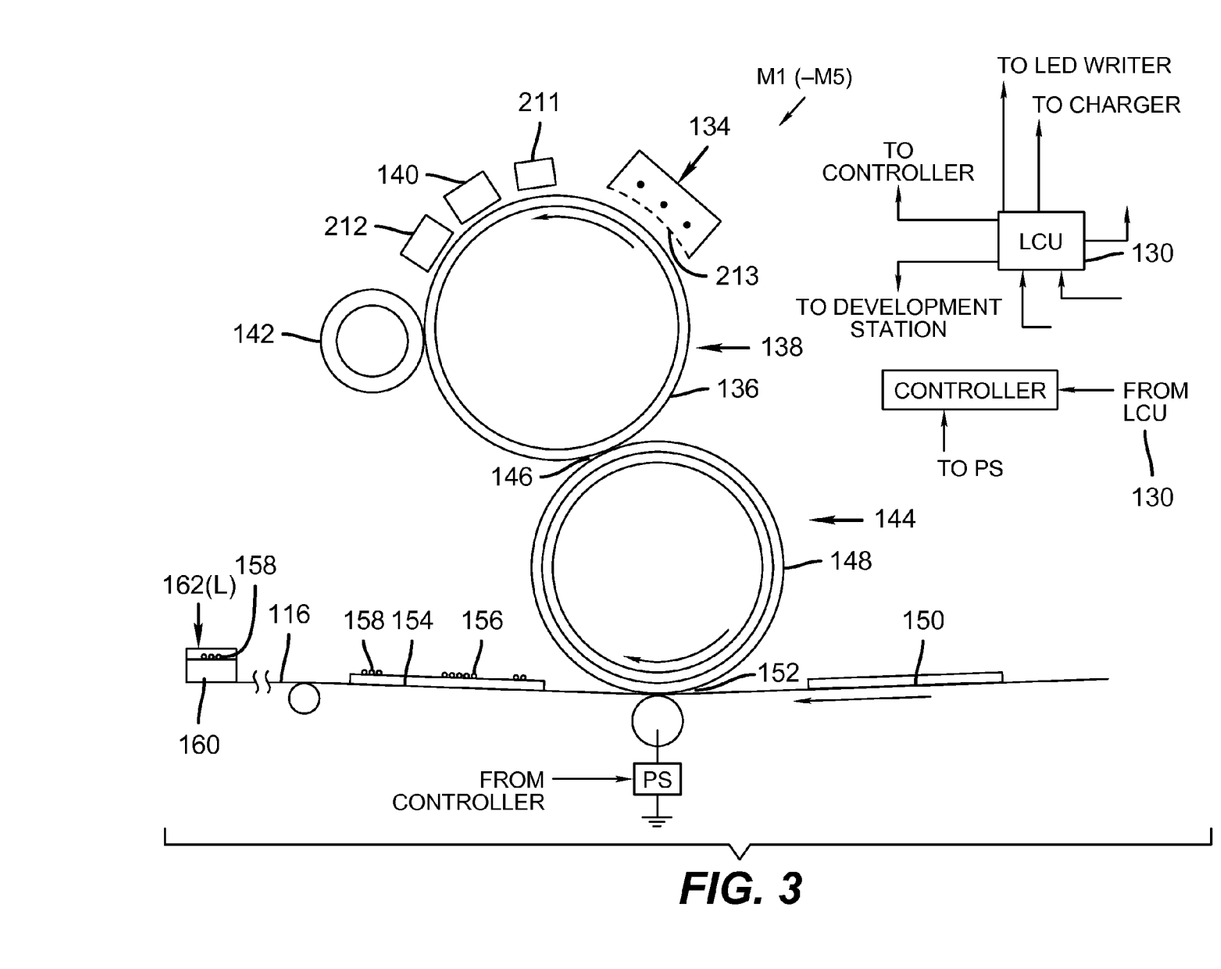
FIG. 3 is a schematic side elevational view, in cross section, of one printing module of the electrographic reproduction apparatus of FIG. 1, on an enlarged scale.

With reference to FIG. 3 wherein a representative printing module (e.g., M1 of M1-M5) is shown, each printing module of the electrographic printer apparatus 100 includes a plurality of electrographic imaging subsystems for producing one or more multilayered image or pattern. Included in each printing module is a primary charging subsystem 134 for uniformly electrostatically charging a surface 136 of a photoconductive imaging member (shown in the form of an imaging cylinder 138). An exposure subsystem 140 is provided for image-wise modulating the uniform electrostatic charge by exposing the photoconductive imaging member to form a latent electrostatic multi-layer (separation) image of the respective layers. A development station subsystem 142 serves for developing the image-wise exposed photoconductive imaging member. An intermediate transfer member 144 is provided for transferring the respective layer (separation) image from the photoconductive imaging member through a transfer nip 146 to the surface 148 of the intermediate transfer member 144 and from the intermediate transfer member 144 to a receiver member (receiver member 150 shown prior to entry into the transfer nip 152 and receiver member 154 shown subsequent to transfer of the multilayer (separation) image) which receives the respective (separation) images 156 in superposition to form a composite image 158 thereon.

Receiver member 160 shown subsequent to the transfer of an additional layer 162 that can be, in one embodiment, A laminate L.

The logic and control unit (LCU) 130 shown in FIG. 3 includes a microprocessor incorporating suitable look-up tables and control software, which is executable by the LCU 130. The control software is preferably stored in memory associated with the LCU 130. Sensors associated with the fusing assembly provide appropriate signals to the LCU 130. In response to sensors S, the LCU 130 issues command and control signals that adjust the heat and/or pressure within fusing nip 108 and otherwise generally nominalizes and/or optimizes the operating parameters of finishing assembly 102 (see FIG. 1) for printing multi-channeled layers in an image 158 on a substrate for as print.

Subsequent to transfer of the respective (separation) multilayered images, overlaid in registration, one from each of the respective printing modules M1-M5, the receiver member is advanced to a finishing assembly 102 (shown in FIG. 1) including one or more fusers 170 to optionally fuse the multilayer toner image to the receiver member resulting in a receiver product, also referred to as a final multi-channeled layer print 175. The finishing assembly 118 may include a sensor 172, an energy source 174 and one or more laminators 110. This can be used in conjunction to a registration reference 176 as well as other references that are used during deposition of each layer of toner, which is laid down relative to one or more registration references, such as a registration pattern.

The laminator 110 may be placed such that the laminate 162 is laid down prior to fusing or after the initial fusing. In one embodiment the apparatus of the invention uses a laminate in one or more layers.

The laminate, in one embodiment, can have a thickness that is greater then the largest toner particle and sufficient to prevent occlusion of the channel in the multi-channeled network. It is important that the laminate, also sometimes referred to as an adhesive film, can go onto of EP created channels without remelting the toner channels.

In one embodiment the material will have residual fusing oil on top, not all adhesive works well in an oiled environment. In that environment the laminate basically has oil absorption capability, so the lamination can be done uniformity on EP printed images. The idea here is 3-D channels (bottom and sides) can be created either via larger toner particle build up as a feature, or via stamping (with features) on thermal remeldable surface, such as coated surfaces.

Alternately, as discussed above the surface texture can be applied early in the printing process. An example is stamping which is essentially a 2-D process. In all the processes it is necessary to close off the channels. Any process that allows the top layer to follow the features below will collapse the channels created and will not work. One workable means is to apply a laminate without too much pressure/heat applied in the finishing steps to created channels in the 10 s micron range as described below.

Figure 4:
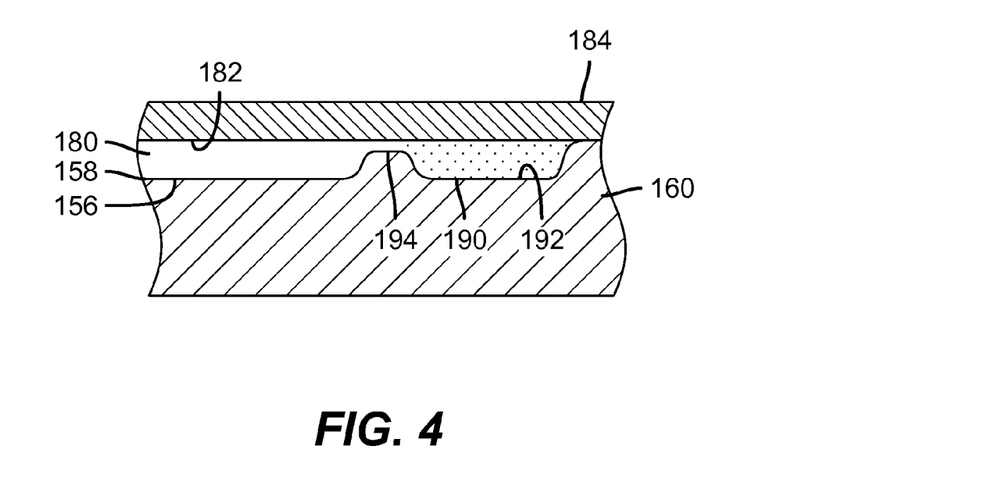
FIG. 4 is a schematic side elevational view, in cross section, of a print, produced by the invention.
Figure 5:
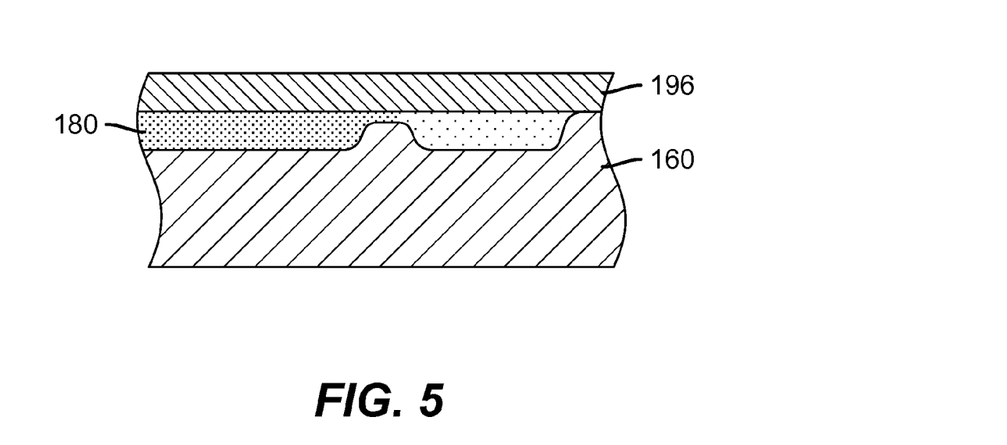
FIG. 5 is a schematic side elevational view, in cross section, of an activated print, having the predetermined multidimensional pattern formed in layers sufficient to form the final predetermined multi-channeled layers produced by the invention.

There are additional advantages to the use of laminates besides forming the top of a channeled network or array. These include improved abrasion resistance, additional types of gloss and increased abrasion and UV protection. It is necessary for the laminate in this invention, or an adhesive film used as a laminate, to have the structural integrity and thickness, as discussed above, to go onto electro photographic created channels without filling the channel when there are finishing actions, such as fusing, which is a remelting of the toner around the channels or the use of fusing oil on top. The laminate must work well in such an environment. One such laminate film is useful for this invention in an electro photographic digital printer and the laminate also has oil absorption capability, so the lamination can be applied uniformly to electro photographic printed images. One such laminate material is A laminate, such as Laminate GBC Layflat with a thickness of 37 um (micron) is useful for this application since the thickness is on the order of magnitude of the desired channel width of 10-50 um that are large enough to allow the toner of less then 8 um to flow. By controlling the laminate thickness the channel is not occluded by distended laminate in that would block the channel. A multiple-channeled layer 180 includes one or more aerially placed channels 182 of variable width but consistent thickness formed on the receiver 160, as shown in FIG. 4. There may be layers of toner laid down between the receiver 160 and the multiple-channeled layer 180. The multiple-channeled layers 180, including the channels 182, are formed prior to the application of a laminate 184. The channel may also include a node 190 that is filled with a movable material 192, such as a fluid or pigment, as well as a narrowed section 194 formed as part of the channel 182. The multiple-channeled layer 180 is capped in one of a few ways including the application of the laminate 184 as described below or laid down as a top layer 196 as shown in FIG. 5, in one or more layers on top of the multiple-channeled layer 180.

The multiple-channeled layer 180 can be made using a larger particle or a chemically prepared toner (CDI) that is useful in building up as a feature as described in a co-pending application for Raised Print U.S. Publication 2008/0159786 hereby incorporated by reference.

The multiple-channeled layer 180 may also be formed as an embossed or varied surface via stamping (with features) on thermal remeldable surface, such as CDI coated surfaces. Two dimension embossing or stamping can create the desired structures needed before the laminate 184 is applied to the multiple-channeled layer 180. Alternatively the paper can have a surface that varies for other reasons that would contribute to the channels structure including a pretreated paper, a paper of higher clay content or having other surface additives that in certain circumstances and conditions achievable in the printing cycle would change the surface profile to form a channel or channels having a pattern, such as a variable and/or periodic pattern.

If the top layer 196 is to be laid down to close off the multiple-channeled layer 180 it involves more then just coating the channel structure with toner such as chemically prepared dry ink (CDI) or an inkjet. The use of different treatable materials must be used so that the finishing processes, including fusing, will not follow the features below and collapse the channels created. If these do not exceed the melting conditions of the top layers needed to create channels, then the multiple-channeled layer 180 will be effectively intact in the final multiple-channeled layer print 160.

Figure 6:
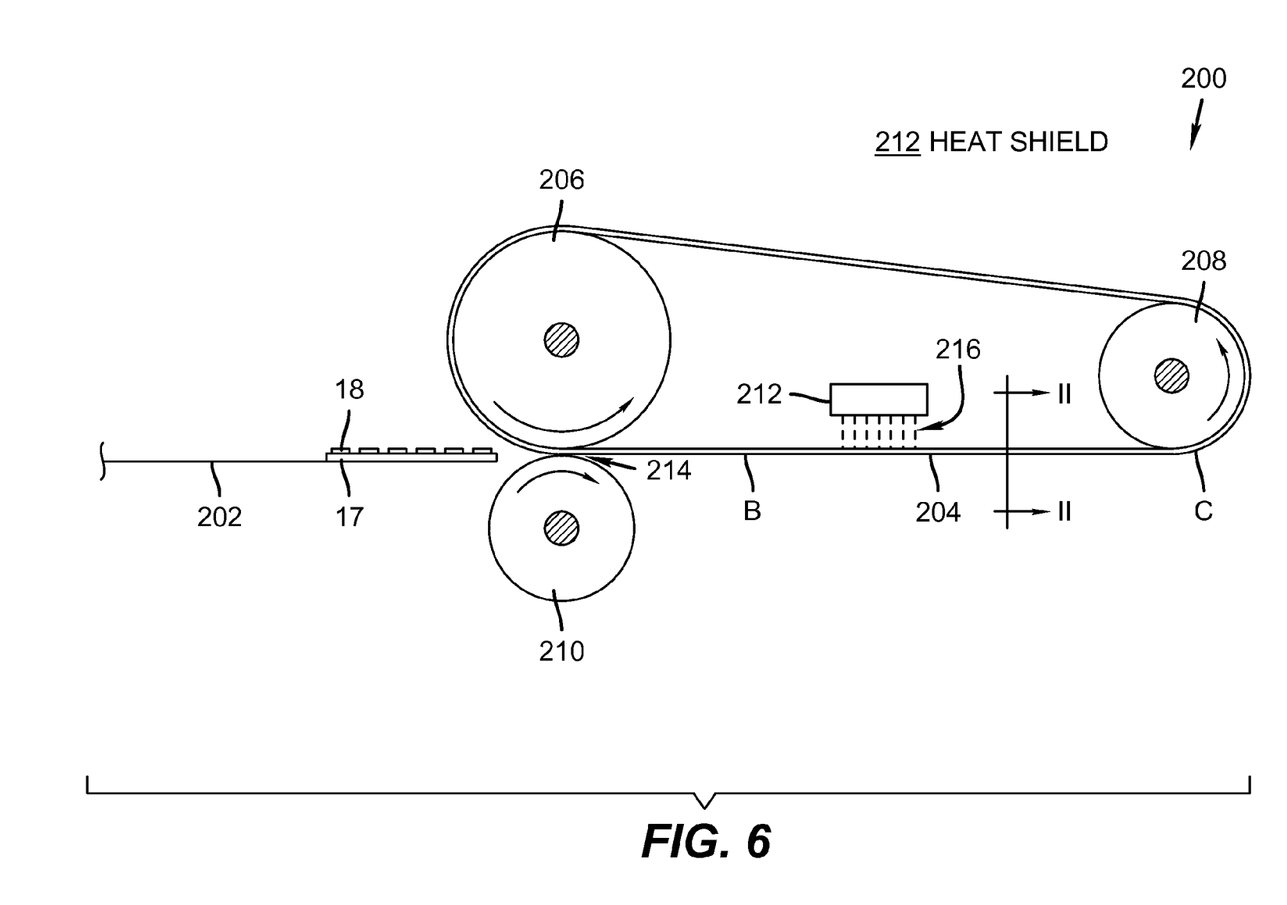
FIG. 6 is a schematic of a portion of the invention of FIG. 1.

One embodiment of the finishing assembly 118 that would allow the top layer to be applied during the fifth module is a type of finishing device 200 shown in FIG. 6. The multiple-channeled layer 180, along with one or more image layers, is transported along a path 202 to the finishing device. The finishing device includes a finishing or fusing belt 204, an optional heated glossing roller 206, a steering roller 208, and a pressure roller 210, as well as a heat shield 212.

The fusing belt 204 is entrained about glossing roller 206 and steering roller 208.

The fusing belt 204 includes a release surface of an organic/inorganic glass or polymer of low surface energy, which minimizes adherence of toner to the fusing belt 204. The release surface may be formed of a silsesquioxane, through a sol-gel process, as described for the toner fusing belt disclosed in U.S. Pat. No. 5,778,295, issued on Jul. 7, 1998, in the names of Jiann-Hsing Chen et al. Alternatively, the fusing belt release layer may be a poly (dimethylsiloxane) or a PDMS polymer of low surface energy, see in this regard the disclosure of U.S. Pat. No. 6,567,641, issued on May 20, 2003, in the names of Muhammed Aslam et al. Pressure roller 210 is opposed to, engages, and forms glossing nip 84 with heated glossing roller 206. Fusing belt 204 and the image bearing receiving member are cooled, such as, for example, by a flow of cooling air, upon exiting the glossing nip 214 in order to reduce offset of the image to the finishing belt 204. Alternately the finishing device could apply a laminate layer 184 and fuse that layer to the multiple-channeled layer 180.

The previously disclosed LCU 130 includes a microprocessor and suitable tables and control software which is executable by the LCU 130. The control software is preferably stored in memory associated with the LCU 130.

Sensors associated with the fusing and glossing assemblies provide appropriate signals to the LCU 130 when the finishing device or laminator is integrated with the printing apparatus. In any event, the finishing device or laminator can have separate controls providing control over temperature of the glossing roller and the downstream cooling of the fusing belt and control of glossing nip pressure. In response to the sensors, the LCU 130 issues command and control signals that adjust the heat and/or pressure within fusing nip 108 so as to reduce image artifacts which are attributable to and/or are the result of release fluid disposed upon and/or impregnating a receiver member that is subsequently processed by/through finishing device or laminator 200, and otherwise generally nominalizes and/or optimizes the operating parameters of the finishing assembly 102 for receiver members that are not subsequently processed by/through the finishing device or laminator 200.

The toner used to form the final multi-channeled layers can be styrenic (styrene butyl acrylate) type used in toner with a polyester toner binder. Typically the refractive index of the polymers used as toner resins have are 1.53 to almost 1.6. These are typical refractive index measurements of the polyester toner binder, as well as styrenic (styrene butyl acrylate) toner. Typically the polyesters are around 1.54 and the styrenic resins are 1.59. The conditions under which it was measured (by methods known to those skilled in the art) are at room temperature and about 590 nm. One skilled in the art would understand that other similar materials could also be used. These could include both thermoplastics such as the polyester types and the styrene acrylate types as well as PVC and polycarbonates, especially in high temperature applications such as projection assemblies. One example is an Eastman Chemical polyester-based resin sheet, Lenstar™, specifically designed for the lenticular market. Also thermosetting plastics could be used, such as the thermosetting polyester beads prepared in a PVA1 stabilized suspension polymerization system from a commercial unsaturated polyester resin at the Israel Institute of Technology.

The toner used to form the final predetermined pattern is affected by the size distribution so a closely controlled size and pattern is desirable. This can be achieved through the grinding and treating of toner particles to produce various resultants sizes. This is difficult to do for the smaller particular sizes and tighter size distributions since there are a number of fines produced that must be separated out. This results in either poor distributions and/or very expensive and poorly controlled processes. An alternative is to use a limited coalescence and/or evaporative limited coalescence techniques that can control the size through stabilizing particles, such as silicon. These particles are referred to as chemically prepared dry ink (CDI) below. Some of these limited coalescence techniques are described in patents pertaining to the preparation of electrostatic toner particles because such techniques typically result in the formation of toner particles having a substantially uniform size and uniform size distribution. Representative limited coalescence processes employed in toner preparation are described in U.S. Pat. No. 4,965,131 hereby incorporated by reference. In one example a pico high viscosity toner, of the type described above, could form the first and or second layers and the top layer could be a laminate or an 8 micron clear toner in the fifth station thus the highly viscous toner would not fuse at the same temperature as the other toner.

In the limited coalescence techniques described, the judicious selection of toner additives such as charge control agents and pigments permits control of the surface roughness of toner particles by taking advantage of the aqueous organic interphase present. It is important to take into account that any toner additive employed for this purpose that is highly surface active or hydrophilic in nature may also be present at the surface of the toner particles.

Particulate and environmental factors that are important to successful results include the toner particle charge/mass ratios (it should not be too low), surface roughness, poor thermal transfer, poor electrostatic transfer, reduced pigment coverage, and environmental effects such as temperature, humidity, chemicals, radiation, and the like that affects the toner or paper. Because of their effects on the size distribution they should be controlled and kept to a normal operating range to control environmental sensitivity.

This toner also has a tensile modulus (103 psi) of 350-1020, normally 345, a flexural modulus (103 psi) of 300-500, normally 340, a hardness of M70-M72 (Rockwell), a thermal expansion of 68-70 10 6/degree Celsius, a specific gravity of 1.2 and a slow, slight yellowing under exposure to light.

This toner also has a tensile modulus (103 psi) of 150-500, normally 345, a flexural modulus (103 psi) of 300-500, normally 340, a hardness of M70-M72 (Rockwell), a thermal expansion of 68-70 10 6/degree Celsius, a specific gravity of 1.2 and a slow, slight yellowing under exposure to light according to J. H. DuBois and F. W. John, eds., in Plastics, 5th edition, Van Norstrand and Reinhold, 1974 (page 522).

In this particular embodiment various attributes make the use of this toner a good toner to use. In any contact fusing the speed of fusing and resident times and related pressures applied are also important to achieve the particular final desired multi-channeled layers. Contact fusing may be necessary if faster turnarounds are needed. Various finishing methods would include both contact and non-contact including heat, pressure, chemical as well as IR and UV.

The described toner normally has a melting range can be between 50-300 degrees Celsius. Surface tension, roughness and viscosity should be such as to yield a better transfer. Surface profiles and roughness can be measured using the Federal 5000 "Surf Analyzer' and is measured in regular unites, such as microns. Toner particle size, as discussed above is also important since larger particles not only result in the desired heights and patterns but also results in a clearer multi-channeled layers since there is less air inclusions, normally, in a larger particle. Toner viscosity is measured by a Mooney viscometer, a meter that measures viscosity, and the higher viscosities will keep an multi-channeled layer's pattern better and can result in greater height. The higher viscosity toner will also result in a retained form over a longer period of time.

Melting point is often not as important of a measure as the glass transition temperature (Tg), discussed above. This range is around 50-100 degrees Celsius, often around 118 degrees Celsius. Clarity, or low haze, is important for multi-channeled layers that are transmissive or reflective wherein clarity is an indicator and haze is a measure of higher percent of transmitted light.

Another embodiment for creating the final multi-channeled layer 180 includes using a patterned paper (like an embossed paper with a specific pattern) and/or pretreated paper. Alternately a patterned roller could be used on the print prior to application of the top layer, along with a non-contact fusing, using a high MW polymer or high viscosity polymer that would not fuse like regular toner and probably a particle size much smaller than normal toner, also possibly metallic toner particles etc. Some papers, such as clay papers, actually will form a channel when heated at a higher temperature, such as during normal during fusing. The use of a clapper with clay content could be used along with a very smooth surface roller to create tiny blisters or micro spaces desired for this embodiment. The regulation of the heat and pressure would be used to control the size and shape of the multi-channels that would become the expansion spaces. Their size would be varied by the application of different amounts of heat and for different lengths of time and in conjunction with different pressures, preferably a low pressure.

In all of these approaches, a toner may be applied to form the final multi-channeled layers desired. It should be kept in mind that texture information corresponding to the toner image plane need not be binary. In other words, the quantity of clear toner called for, on a pixel by pixel basis, need not only assume either 100% coverage or 0% coverage; it may call for intermediate "gray level" quantities, as well.

It is important to be able to create channels in a digital fashion when customization is desired. For chromatography of a sample, not only the nature of the packing material is important, but also the length of the column. Many analytes can be separated with a short column while some may require a long column. In some cases multiple columns containing different packing materials is required. It is obviously beneficial to be able to change the path length as well as location simply for different applications. This invention has the flexibility to fulfill this need.

Figure 7:
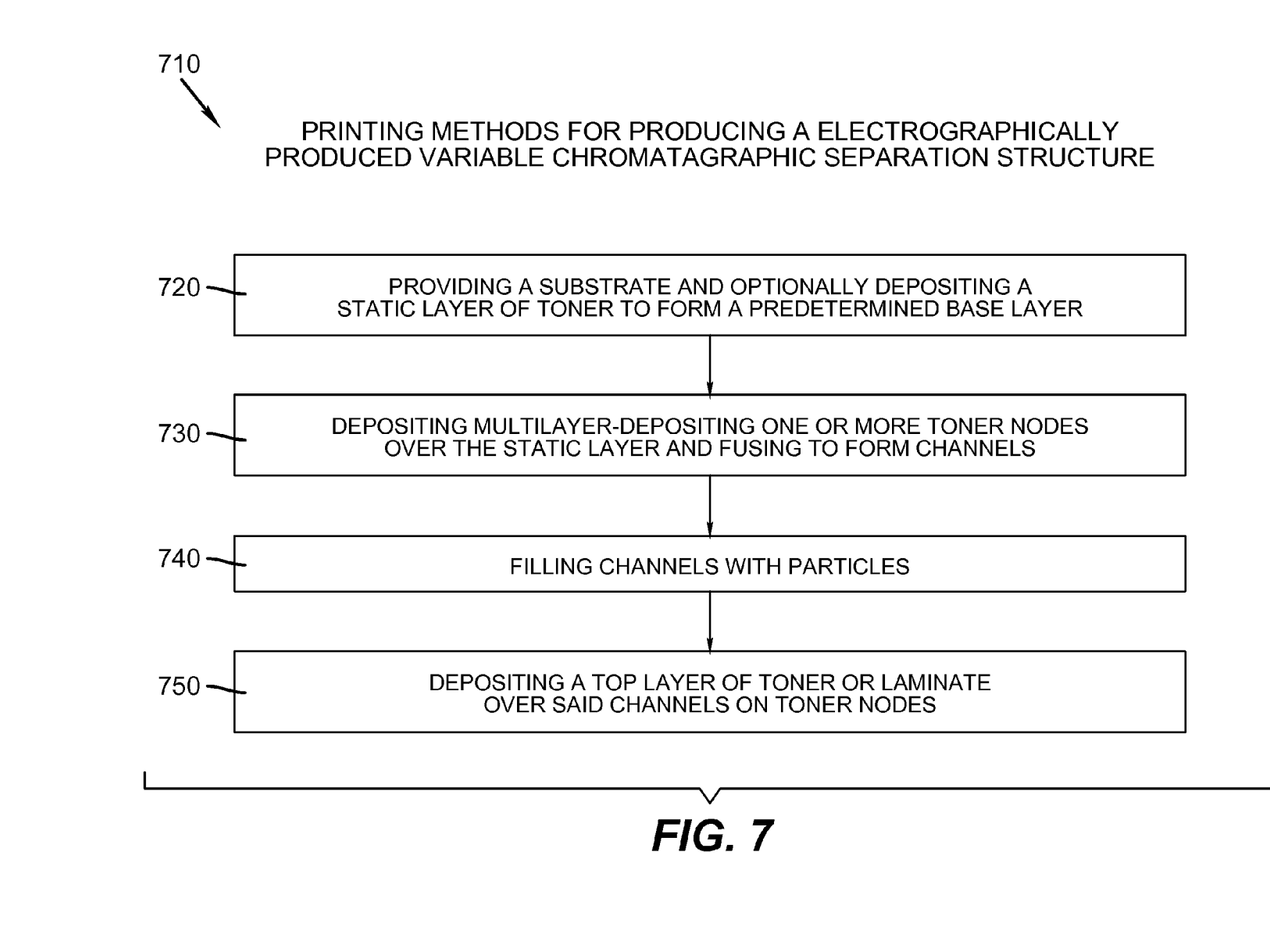
FIG. 7 is an embodiment of a digital method of printing a chromatographic separator column.

Referring to FIG. 7, a flow chart is shown for the printing method for producing an electrographically produced variable chromatographic separation structure 710. In the first step 720 a static layer of toner is deposited to form a predetermined base layer. This step is optional if an appropriately configured substrate is provided. In step two 730, one or more layers of toner nodes are deposited over the static layer and fused to form channels. These channels can be a multi-channel layer defining an expansion space that includes one or more channels. In step three 740 the channels are filled with material, such as particulate material or particles which have the property of slightly interacting with the material to be separated. In the last step 750, a layer of toner is deposited or a laminate sheet is applied over the device. Toner is fused and/or the laminate is fixed to provide a cover for the channels.

The step three 740 that places, such as by pumping a material or movable material such as a fluid into the one or more channels. This can be accomplished in a number of ways. A preferred method for filling of the packing material is the application via gravity as a dry powder and then leveled to the tops of the channels with a knife in a squeegee fashion. This would give a level surface with the tops of the channels essentially clean. The cleanliness of the tops of the channels is only important in so far as giving the ability to adhere the top encapsulation in a pinhole free manner. If pinholes are generated along the top of the channel in the next step, inter-mixing and/or sample loss may occur. In one embodiment the channels can be capped or have bathers introduced that create one or more internally packed channel structures prior to pumping movable materials into them. A sensor downstream can help with these stops.

Another method for applying the packing material is via slurry coating, drying, and then squeegeeing the surface as previously discussed. The advantage here is that the slurry will tend to fall into the channels and fill it preferentially.

Another method which may be desirable when more than one column is desired is to patternwise apply the particles by the electrographic process. This works for chargeable particles and has the advantage of being very efficient and conserves materials. This will require the alignment of the sample with the packing material particle image.

Another embodiment is to provide the material is a slurry at the nip during lamination and force the material into the channels as the lamination of an encapsulate is occurring. In this manner solvent is entrapped which may be removed or may be maintained for future use in the device.

The packing material is may be any particulate material which has an affinity with materials to be separated. Some examples which are often used in columns as packing material are silica, alumina, carbon and resins. It will be appreciated that the number of material which can be used is large and is dependent on the exact application.

One embodiment of the encapsulant is as a laminate. The laminate can be any material which does not interact with the solvent and can be adhered to the tops of the channels. It can include a thermal adhesive or a pressure sensitive adhesive or simple be directly fusable with the channel.

Figure 8:
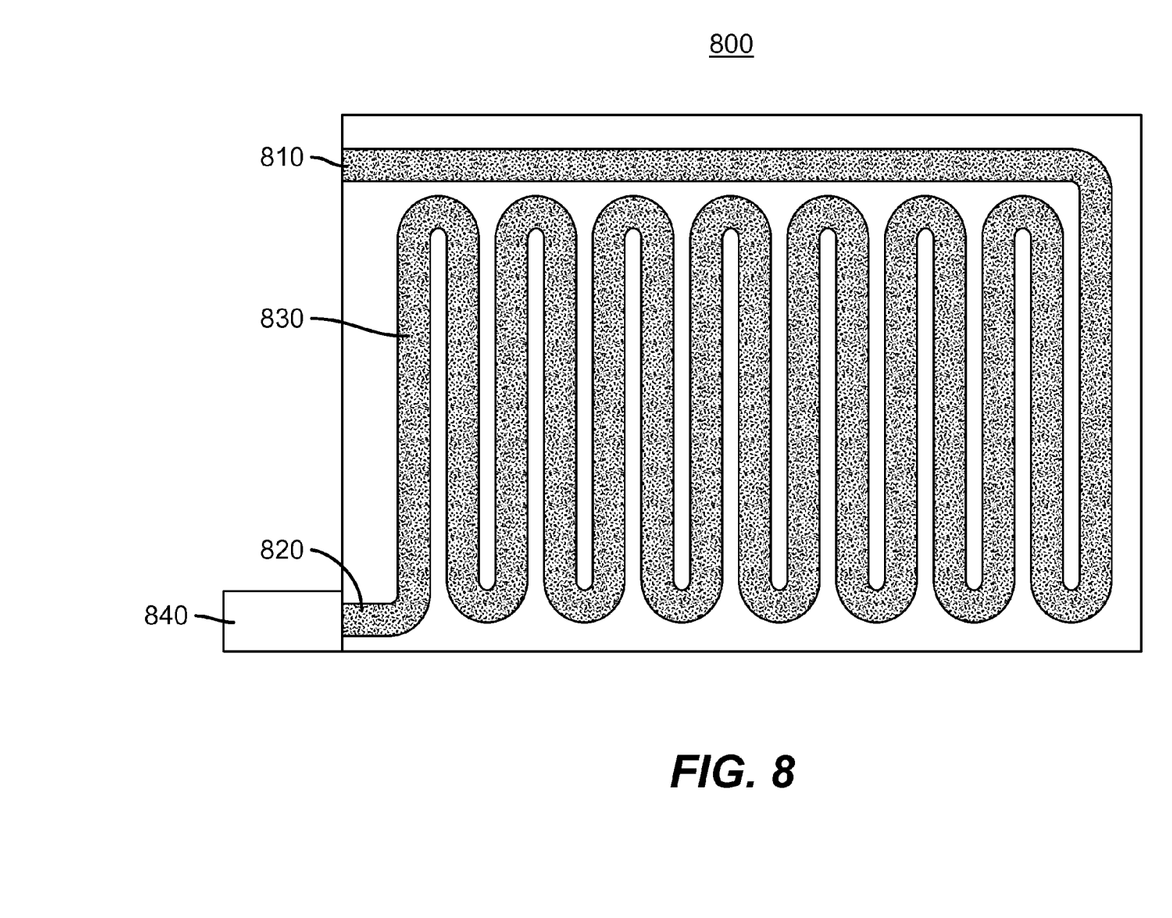
FIG. 8 is a schematic top view of a chromatographic column, produced by the method of FIG. 7.

Referring to FIG. 8, a top view of a chromatographic device 800 of the invention is shown. An entrance port 810 on the device is where either a liquid or gas can be introduced. In one embodiment with for a limited use device, the fluid is already on the device in a reservoir and there is no need for an entrance port. The channels packed with particles 830 wind around the device to increase the effective length. When a fluid travels through the entrance port 810 it will wind through the channels packed with particles eventually arriving at the exit port 820.

A sensor 840 is often placed at the exit port 820 to monitor the fluid and solvates leaving. The sensor can be any of a number of devices to distinguish the passage of a material. Examples include UV, visible and IR detector as well as thermal and conductivity detectors. Any detector which can distinguish a change when the fluid carrier traverses with a solute molecule could be used.

Figure 9:
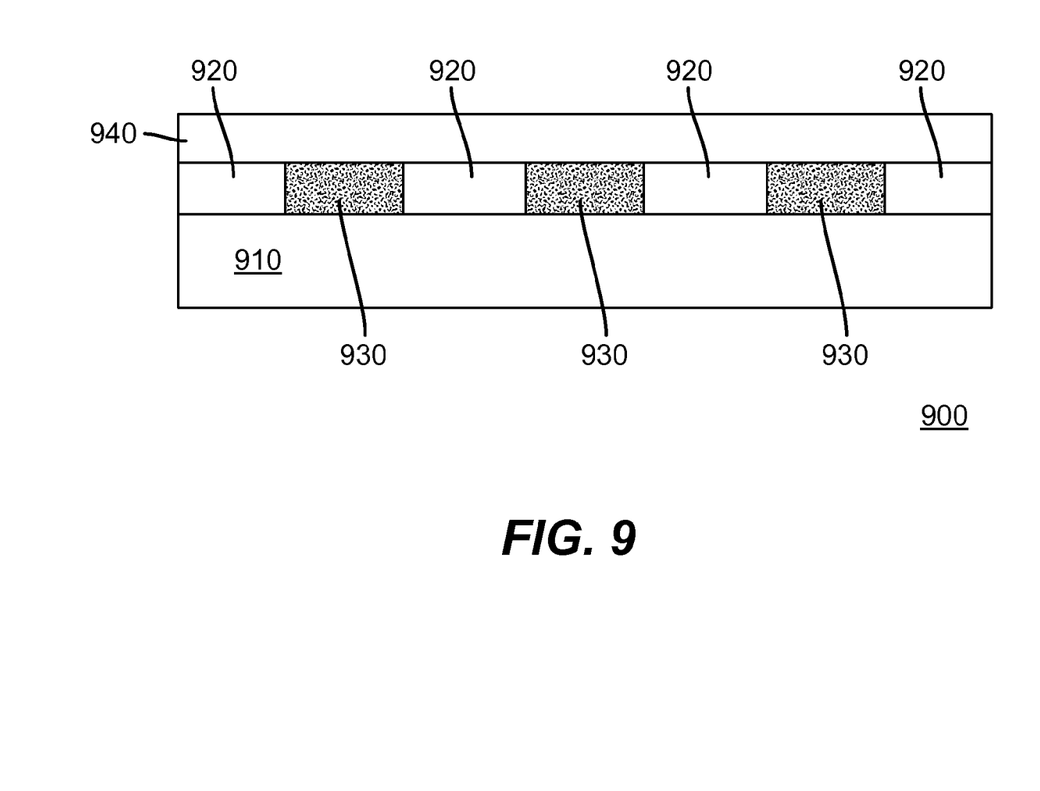
FIG. 9 is a schematic side view of a waveguide, produced by of the method of FIG. 7.

In FIG. 9 is shown a cross section of the device 900 of the invention. The substrate 910 is shown with electrographically deposited channel walls 920. Between the walls are the channels packed with particles 930. Finally we see the encapsulate 940 covering the top side if the channels packed with particles 930. In this manner one can see that that liquid can flow the channels packed with particles and slowly any solvate will be retarded in its travels by binding with the particles.

In another embodiment the sensors are detectors that are present in the structure itself. Also present can be one or more mixing chambers and other microfluidic devices. These make the single device structure a complete device capable of operating as a single chromophic column for example. In this case, the exit port may be for waste after detection and other processes have occurred.

In another embodiment for limited use or single use applications, there may be no exit port. The material to be analyzed is pumped through the column and into a reservoir for storage. The device, containing the waste reservoir, is then disposed of. In this manner no waste fluids need be handled.

The invention has been described in detail with particular reference to certain preferred embodiments thereof, but it will be understood that variations and modifications can be effected within the spirit and scope of the invention.

What is claimed is:

1. A printing method of manufacturing a chromatographic column structure comprising:
   depositing a static layer of toner to form a predetermined multi-channeled layer;
   depositing a second layer of one or more toner nodes over the static layer;
   depositing a top layer of laminate over said toner nodes, said top layer and the multi-channeled layer defining an expansion space, including one or more channels, adjacent said toner nodes;
   filling the one or more channels with a particulate material that has an affinity with a material to be separated from any fluid that is pumped into the channels;
   fusing the toners to form a fused toner channels with nodes that are bonded to the top laminate with the particulate material in the fused toner channels;
   and
   wherein the toner channels include an entrance port through which a fluid having the material to be separated can be pumped though the particulate material in the one or more channels.

2. The method of claim 1 wherein the movable material is a fluid that is pumped through the entrance port and an exit port.

3. The method of claim 1 further comprising capping the channels to create one or more internally packed channel structures prior to pumping the movable material.

4. The method of claim 3 wherein the movable material is a solvent, that interacts with the material in the one or more internally packed channel structures during the pumping step.

5. The method of claim 1 further comprises a sensor at a down flow point.

6. The method of claim 1 further comprises activating the material in the one or more channels to create a resultant material with different characteristics.

7. The method of claim 1 wherein the material is one or more of a silica, alumina, carbon and resin.

8. The method of claim 1 wherein the pumping step includes applying a slurry.

9. The method according to claim 1 further comprises laying down a continuous static layer of toner to form one or more non-continuous expansion spaces.

10. A printing method of manufacturing a particulate filter comprising:
    depositing a static layer of toner to form a predetermined multi-channeled layer;
    depositing a second layer of one or more toner nodes over the static layer;
    depositing a top layer of laminate over said toner nodes, said top layer and the multi-channeled layer defining an expansion space, including one or more channels, adjacent said toner nodes;
    filling the one or more channels with a particulate material that has an affinity with a material to be separated from any fluid that is pumped into the channels; and
    fusing the toners to form a fused toner channels with nodes that are bonded to the top laminate with the particulate material in the fused toner channels;
    and
    wherein the toner channels include an entrance port through which a fluid having the material to be separated can be pumped though the particulate material in the one or more channels.

11. The method of claim 10 further comprising capping the channels to create one or more internally packed channel structures prior to pumping the movable material.

12. The method of claim 11 wherein the movable material is a solvent, that interacts with the material in the one or more internally packed channel structures during the pumping step.

13. The method of claim 10 further comprises a sensor at a down flow point.

14. The method of claim 10 wherein the particulate material is one or more of a silica, alumina, carbon, and resin.

15. The method of claim 10 wherein the pumping a movable material step includes a slurry is applied.

16. The method of claim 15 further comprising coating, drying and squeegeeing the one or more channels.

17. A method for electrographic printing of one or more multi-channeled layers upon a receiver, said printing comprising the steps of:
    depositing a static layer of toner to form a predetermined multi-channeled layer;
    depositing a second layer of one or more toner nodes over the static layer;
    depositing a top layer of laminate over said toner nodes, said top layer and the multi-channeled layer defining an expansion space, including one or more channels, adjacent said toner nodes;
    filling the one or more channels with a particulate material that has an affinity with a material to be separated from any fluid that is pumped into the channels;
    fusing the toners to form a fused toner channels with nodes that are bonded to the top laminate with the particulate material in the fused toner channels;
    and
    wherein the toner channels include an entrance port through which a fluid having the material to be separated can be pumped though the particulate material in the one or more channels.

18. The method of claim 17 wherein the particulate material is a chargeable particle.

19. The method of claim 17 further comprises capping the channels to create one or more internally packed channel structures prior to pumping the movable material.

20. The method of claim 19 wherein the movable material is a fluid, such as a solvent, that interacts with the material in the one or more internally packed channel structures during the pumping step.

* * * * *